(12) United States Patent
Eng

(10) Patent No.: US 8,080,698 B2  
(45) Date of Patent: Dec. 20, 2011

(54) METHOD FOR OLEFIN PRODUCTION FROM BUTANES AND CRACKING REFINERY HYDROCARBONS AND ALKANES

(75) Inventor: Curtis N. Eng, Sugar Land, TX (US)

(73) Assignee: Kellogg Brown & Root LLC, Houston, TX (US)

(*) Notice: Subject to any disclaimer, the term of this patent is extended or adjusted under 35 U.S.C. 154(b) by 788 days.

(21) Appl. No.: 11/927,857

(22) Filed: Oct. 30, 2007

(65) Prior Publication Data

US 2009/0112039 A1  Apr. 30, 2009

(51) Int. Cl.
*C07C 4/02* (2006.01)

(52) U.S. Cl. ........ 585/324; 585/327; 585/613; 585/618; 585/639; 585/648; 585/654

(58) Field of Classification Search .................. None
See application file for complete search history.

(56) References Cited

U.S. PATENT DOCUMENTS

| | | | |
|---|---|---|---|
| 3,580,837 A | 5/1971 | Pollitzer et al. | |
| 4,997,545 A | 3/1991 | Krishna et al. | |
| 5,043,522 A | 8/1991 | Leyshon et al. | |
| 5,198,590 A | 3/1993 | Sofranko et al. | |
| 5,200,059 A * | 4/1993 | Bogdan et al. ................ 208/79 |
| 5,215,650 A | 6/1993 | Sapre | |
| 5,254,748 A | 10/1993 | Hensley et al. | |
| 5,307,117 A | 4/1994 | Harlan | |
| 5,446,224 A | 8/1995 | Miracca et al. | |
| 5,523,502 A | 6/1996 | Rubin | |
| 5,944,982 A | 8/1999 | Lomas | |
| 6,049,017 A * | 4/2000 | Vora et al. ................... 585/324 |
| 6,069,287 A | 5/2000 | Ladwig et al. | |
| 6,287,522 B1 | 9/2001 | Lomas | |
| 6,339,181 B1 | 1/2002 | Chen et al. | |
| 6,538,169 B1 | 3/2003 | Pittman et al. | |
| 6,977,321 B1 | 12/2005 | Dath et al. | |
| 7,128,827 B2 | 10/2006 | Tallman et al. | |

* cited by examiner

*Primary Examiner* — Tam M Nguyen

(57) ABSTRACT

Systems and processes for producing one or more olefins are provided. A feed containing $C_4$ compounds can be dehydrogenated to provide a first product containing butene. At least a portion of the first product can be bypassed around a methyl-tert-butyl-ether production unit and cracked in a first cracker to provide a second product containing propylene, ethylene, and butane. A light hydrocarbon containing gas oils, full range gas oils, resid or any combination thereof can be cracked in a second cracker to provide a cracked hydrocarbon containing propylene, ethylene, and butane. An alkane can be cracked in a third cracker to provide cracked alkanes containing propylene, ethylene, and butane. The second product, cracked hydrocarbons, and cracked alkanes can be combined and separated to provide a third product containing propylene and a first recycle containing butane. At least a portion of the first recycle can be recycled to the first product prior to cracking. At least a portion of the first recycle can be recycled to feed prior to dehydrogenation.

30 Claims, 2 Drawing Sheets

METHOD FOR OLEFIN PRODUCTION FROM BUTANES AND CRACKING REFINERY HYDROCARBONS AND ALKANES

BACKGROUND

1. Field

The present embodiments generally relate to systems and processes for producing olefins from hydrocarbon mixtures containing one or more butanes.

2. Description of the Related Art

Methyl tert-butyl ether ("MTBE") is manufactured by the chemical reaction of methanol and isobutene for primary use in gasoline. MTBE is a common component in reformulated fuels developed to reduce smog and meet Clean Air Act goals. MTBE has been produced in very large quantities for use as a gasoline additive since about 1979.

However, MTBE production has decreased as various jurisdictions restricted or banned its use. By late 2006 most American gasoline retailers stopped using MTBE as an oxygenate. Accordingly, domestic production has continued to decline. As a result, MTBE manufacturers are left holding useless feedstocks and manufacturing assets.

There is a need, therefore, for reallocating feedstocks and manufacturing assets previously allocated to the manufacture of MTBE, thereby providing an economic benefit to MTBE manufacturers.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
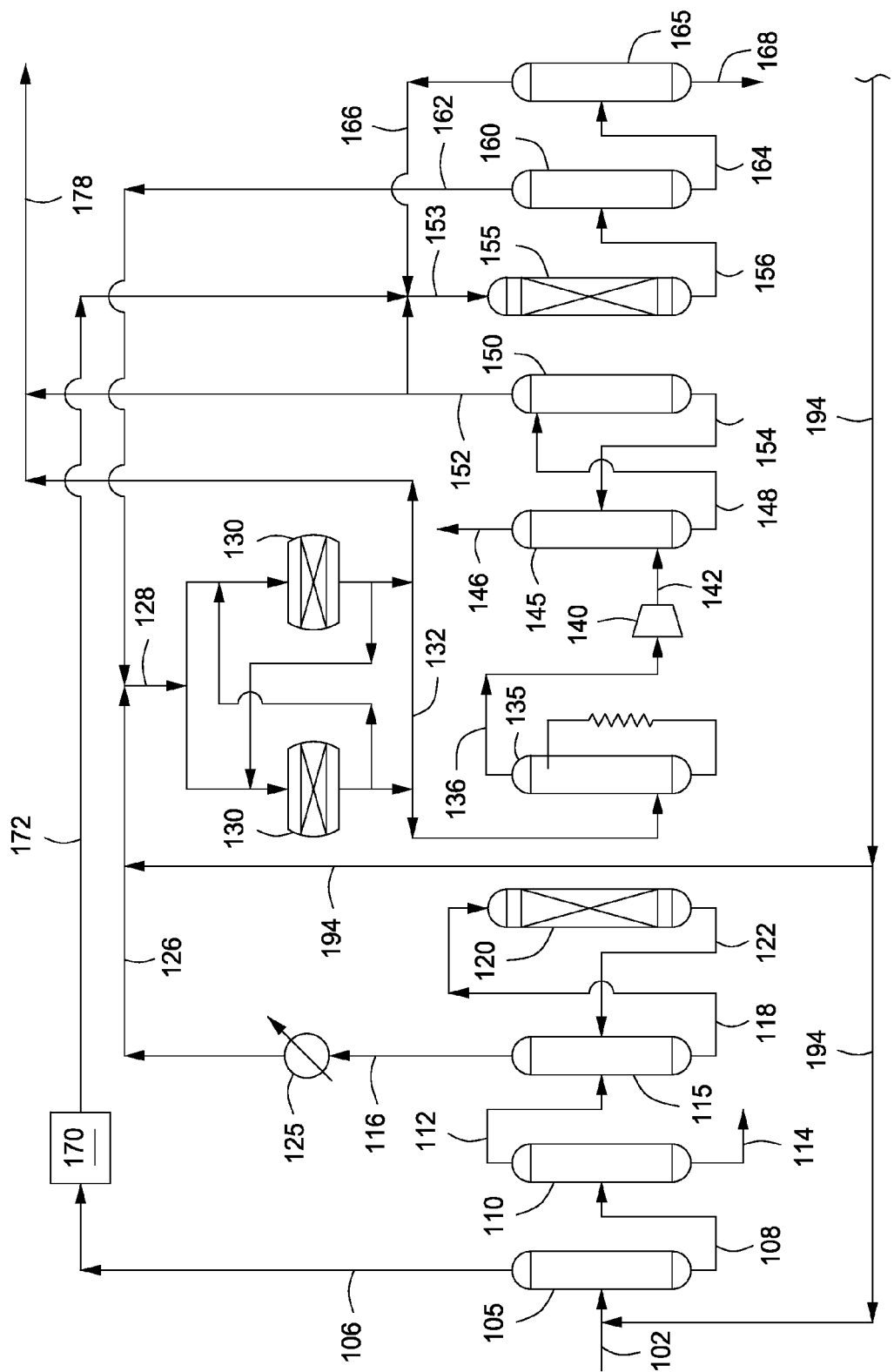
FIG. 1 depicts an illustrative system for producing a $C_4$-containing feedstock according to one or more embodiments described.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology.

Systems and processes for producing a $C_4$-containing feedstock and/or one or more olefins are provided. In one or more embodiments, a hydrocarbon mixture containing one or more $C_4$ compounds can be a feedstock to produce one or more olefins including ethylene and propylene. In one or more embodiments, butane intermediates from an existing methyl tert-butyl ether ("MTBE") process can be used as the feedstock. For example, an existing MTBE system can be retrofitted or converted to provide the feedstock for producing the one or more olefins.

In at least one specific embodiment, A feed comprising butane can be dehydrogenated to provide a first product comprising butene. The first product can be direct or bypassed around an etherification reactor for converting isobutylene to methyl tert-butyl ether. At least a portion of the first product can be cracked in a first cracker to provide a second product comprising propylene, ethylene, and butane. A refinery hydrocarbon comprising gas oil, full range gas oil, resid, or a combination thereof and/or a light hydrocarbons can be cracked in a second cracker to provide a cracked hydrocarbon comprising ethylene, propylene, or a combination thereof. One or more alkanes can be cracked in a third cracker to provide an effluent comprising ethylene and propylene. The second product, cracked hydrocarbons, and cracked alkanes can be combined and separated to provide a third product containing propylene and a first recycle containing butane. At least a portion of the first recycle can be recycled to the first product prior to cracking. At least a portion of the first recycle can be recycled to feed prior to dehydrogenation.

The term "light hydrocarbon" as used herein refers a hydrocarbon having a carbon number less than or equal to 4.

The term "naphtha" as used herein refers to a mixture of one or more hydrocarbons, where less than 10% wt of the mixture vaporizes at a temperature less than 175° C., and more than 95% wt of the mixture vaporizes at a temperature 1 less than 240° C., as determined by ASTM standard method D86.

The term "heavy naphtha" as used herein refers to a fraction with a boiling temperature from about 166° C. to about 211° C.

The term "BTX" as used herein refers to a hydrocarbon mixture having at least benzene, toluene, and xylene, mixtures thereof or combinations thereof.

FIG. 1 depicts an illustrative system for producing a $C_4$-containing feedstock according to one or more embodiments. In one or more embodiments, a feedstock via line 102 can be selectively separated using one or more separators 105, 110, 115 and/or 120, and dehydrogenated using one or more dehydrogenation reactors 130, to provide a first product in line 132. A first portion of the first product can be used to produce one or more olefins via line 178, while a second portion of the first product can be further processed using one or more columns 135, 145, and 150 to provide a purified isobutenes and isobutanes via line 152. In one or more embodiments, a first portion of the isobutenes and isobutanes via line 152 can form a feedstock for olefin production via line 178, while a second portion of the isobutenes and isobutanes via line 152 can form a feedstock for MTBE production using one or more etherification reactors 155 and pressure columns 160, 165.

In one or more embodiments, the feedstock via line 102 can consist essentially of light hydrocarbons. In one or more embodiments, the feedstock can include, but is not limited to, one or more $C_4$-containing compounds such as butane (i.e. "n-butane") and isobutane. In one or more embodiments, the feedstock can be a refinery off-gas resulting from the distillation of crude oil. In one or more embodiments, the feedstock via line 102 can include from about 1% vol to 5% vol methane, from about 1% vol to about 10% vol ethane, from about 1% vol to about 30% vol propane, from about 1% vol to about 35% vol butane, and from about 1% vol to about 20% vol heavier hydrocarbons. In one or more embodiments, the feedstock via line 102 can be introduced to the one or more rectifier columns 105 at a temperature of about 25° C. to about 200° C.

In one or more embodiments, the $C_4$ and heavier hydrocarbons via line 108 can include from about 50% vol to about 95% vol $C_4$, from about 1% vol to about 25% vol $C_5$, from about 1% vol to about 10% vol $C_6$, and from about 1% vol to about 5% vol $C_7$ and/or heavier hydrocarbons. In one or more embodiments, the $C_4$ and heavier hydrocarbons via line 108 can include at least about 25% vol to about 95% vol $C_4$.

The feedstock, via line 102, can be introduced to the one or more rectifier columns 105 and selectively separated therein to provide an overhead containing $C_1$-$C_3$ hydrocarbons via line 106 and a bottoms containing $C_4$ and heavier hydrocarbons via line 108. In one or more embodiments, at least a portion of the $C_1$-$C_3$ hydrocarbons in the overhead 106 can be directed to a methanol unit 170 to provide methanol via line 172. Although not shown in FIG. 1, at least a portion of the $C_1$-$C_3$ hydrocarbons in the overhead 106 can be used as a feedstock for reforming, and/or fractionated to provide fungible products such as methane, ethane and propane. In addition to $C_1$-$C_3$ hydrocarbons, the overhead via line 106 can contain at least 1% vol methane. In one or more embodiments, the overhead via line 106 can have as much as 10% vol methane. The overhead via line 106 can include at least 5% vol propane. In one or more embodiments, the overhead via line 106 can include from about 1% vol to 10% vol methane, from about 5% vol to 70% vol ethane, and from about 5% vol to 70% vol propane.

The one or more rectifier columns 105 can be any system or device or combination of systems and/or devices suitable for separating the feedstock via line 102 into an overhead containing $C_1$-$C_3$ hydrocarbons via line 106 and a bottoms containing $C_4$ and heavier hydrocarbons via line 108. In one or more embodiments, the one or more rectifier columns 105 can have packing media to provide surface area to facilitate separation of the feedstock via line 102. For example, the packing media can include rings, saddles, balls, irregular sheets, tubes, spirals, trays, plates, and/or baffles. In one or more embodiments, the one or more rectifier columns 105 can operate at pressures ranging from about 100 kPa to about 2000 kPa, about 1000 kPa to about 2000 kPa, about 200 kPa to about 1000 kPa, or about 100 kPa to about 200 kPa. Each rectifier column 105 can operate at temperatures ranging from about −10° C. to about 300° C., about 100° C. to about 300° C., about 20° C. to about 100° C., or about −10° C. to about 50° C.

In one or more embodiments, the $C_4$ and heavier hydrocarbons via line 108 can be introduced to one or more de-butanizing columns 110 and selectively separated therein to provide an overhead containing $C_4$ hydrocarbons via line 112 and a bottoms containing $C_5$ and heavier hydrocarbons via line 114. In one or more embodiments, the overhead 112 can include butane and/or isobutane. In one or more embodiments, the overhead 112 can include at least about 30% vol, at least about 40% vol, at least about 50% vol, at least about 60% vol, or at least about 70% vol butane. In one or more embodiments, the overhead 112 can include at least about 30% vol to 70% vol butane and at least about 70% vol to 30% vol isobutane.

The $C_5$ and heavier hydrocarbons via line 114 can exit the de-butanizing column 110 at a temperature of about 25° C. to about 200° C. depending on the pressure maintained within the column 110. For example, the pressure can be from about 50 kPa to about 1500 kPa. In one or more embodiments, the bottoms 114 can include at least about 70% wt, 80% wt, or 90% wt $C_5$, up to about 30% wt $C_6$, and up to about 10% wt $C_7$ and heavier hydrocarbons. Although not shown in FIG. 1, the bottoms 114 can be used as a feed for one or more cracking units including, but not limited to, thermal cracking, steam pyrolytic cracking, hydrocracking, fluid catalytic cracking or any series or parallel combination thereof.

The de-butanizing column 110 can be any device suitable for selectively separating $C_5$ and heavier hydrocarbons. In one or more embodiments, the de-butanizing column 110 can include packing media to facilitate separation of the hydrocarbons. For example, the de-butanizing column 110 can include rings, saddles, balls, irregular sheets, tubes, spirals, trays, plates, and/or baffles.

In one or more embodiments, the overhead 112 can be introduced to one or more de-isobutanizing columns 115 and selectively separated therein to provide an overhead line 116 that contains primarily isobutane and a bottoms 118 that contains primarily butane. In one or more embodiments, the overhead 116 can contain about 70% vol or more, about 80% vol or more, about 90% vol or more, or about 95% vol or more isobutane. In one or more embodiments, the overhead 116 can include from about 5% vol to about 30% vol butane and from about 70% vol to about 99% vol isobutane. The temperature of the overhead 116 can be about 10° C. to about 150° C., and the pressure can be from about 50 kPa to about 1500 kPa.

In one or more embodiments, the bottoms 118 can include about 70% vol to about 99% vol butane. For example, the bottoms 118 can include from about 60% vol to about 90% vol; about 60% vol to about 70% vol; about 70% vol to about 80% vol; or about 80% vol to about 90% vol butane. The bottoms 118 can also include about 5% vol to about 30% vol, about 5% vol to about 10% vol, about 10% vol to about 20% vol, or about 20% vol to about 30% vol isobutane. The temperature of the bottoms 118 can be about 10° C. to about 150° C., and the pressure can be about 50 kPa to about 1500 kPa.

The de-isobutanizing column 115 can be any device, system or combination of devices and/or systems suitable for selectively separating the $C_4$ hydrocarbons via line 112 into an overhead containing primarily isobutane and a bottoms containing primarily butane. In one or more embodiments, the de-isobutanizing column 115 can include packing media to facilitate separation of the hydrocarbons. For example, the de-isobutanizing column 115 can include rings, saddles, balls, irregular sheets, tubes, spirals, trays, plates, and/or baffles. In one or more embodiments, the de-isobutanizing column 115 can have at least 10 to 25, 20 to 35, 30 to 45, 40 to 55, 50 to 65, 60 to 75, 70 to 85, 80 to 95, or 90 to 100 plates. The de-isobutanizing column 115 can operate at temperatures from about 60° C. to about 90° C., from about 65° C. to about 85° C., or from about 70° C. to about 80° C. In one or more embodiments, the de-isobutanizing column 115 can operate at pressures from about 800 kPa to about 1400 kPa, from about 800 kPa to about 1300 kPa, from about 800 kPa to about 1200 kPa, or from about 900 kPa to about 1200 kPa.

In one or more embodiments, the bottoms 118 can be introduced to one or more reactors 120 to isomerize butane to isobutane. In one or more embodiments, the bottoms 122 that contains butane and some amount of non-isomerized isobutane can have an isobutane to total butanes ratio ranging from 0.45 to 0.75, depending upon the operating temperature of the one or more isomerization reactors 120. The bottoms 122 can be recycled to the de-isobutanizing column 115 for further separation. Although not shown, the bottoms 122 can be selectively separated using a fractionation column to remove any lighter hydrocarbons, thereby increasing the $C_4$ concentration, and the separated $C_4$ hydrocarbons can be returned to the de-isobutanizing column 115 for further processing.

The one or more isomerization reactors 120 can include any device, system or combination of systems and/or devices suitable for converting at least a portion of the butane to isobutane. In one or more embodiments, each isomerization reactor 120 can convert about 5 mol % to 40 mol %, about 5 mol % to 15 mol %, about 10 mol % to 20 mol %, about 15 mol % to 25 mol %, about 20 mol % to 30 mol %, about 25 mol % to 35 mol %, or about 30 mol % to 40 mol % of the butane in the overhead 118 to isobutane. In one or more embodiments, the isomerization reaction can occur at a pressure of about 1000 kPa to about 3800 kPa, about 1200 kPa to about 3400 kPa, or about 1400 kPa to about 2800 kPa. The isomerization reaction can occur at a temperature of about 150° C. to about 205° C., about 150° C. to about 200° C., about 150° C. to about 195° C., about 150° C. to about 190° C., about 150° C. to about 185° C., or about 150° C. to about 180° C.

In one or more embodiments, the temperature of the isobutane via line 116 can be increased using one or more heat exchangers 125 to provide warmer isobutane ("feed") via line 126. In one or more embodiments, the isobutane via line 126 can be heated to the temperature necessary for dehydrogenation of the isobutane, such as about 500° C. to about 650° C. The heat exchanger 125 can be a shell and tube type, plate type, fired heater, regenerative type heat exchanger, air heater, or any combination thereof.

In one or more embodiments, the feed via line 126 can be introduced to one or more dehydrogenation reactors 130. In one or more embodiments, the isobutane via line 126 can be combined with any other available isobutanes, such as those available from the MTBE production unit via line 162, to provide a dehydrogenation feed via line 128. In one or more embodiments, the dehydrogenation feed via line 128 can include isobutane, butane, mixtures thereof, derivatives thereof, or combinations thereof. In one or more embodiments, the dehydrogenation feed via line 128 can include one or more $C_4$ compounds with varying ratios of isobutane and butane. In one or more embodiments, the dehydrogenation feed via line 128 can have an isobutane concentration ranging from about 50% vol to about 99% vol; about 60% vol to about 90% vol; or from about 70% vol to about 80% vol. In one or more embodiments, the dehydrogenation feed via line 128 can include about 40% wt to about 90% wt olefinic compounds having 4 or more carbon atoms and about 5% wt to about 60% wt paraffinic compounds having 4 or more carbon atoms. In one or more embodiments, the temperature of the dehydrogenation feed via line 128 can be from about 500° C. to about 650° C. The pressure of the dehydrogenation feed via line 128 can be from about 10 kPa to about 300 kPa.

The dehydrogenation feed via line 128 can be equally or unequally apportioned to the one or more dehydrogenation reactors 130 (two are shown) where at least a portion of the isobutane therein can be converted to isobutene, providing a first product via line 132. In one or more embodiments, the first product can include at least 90% wt $C_4$-$C_{10}$ hydrocarbons. In one or more embodiments, the first product can include of from about 5% wt to about 90% wt $C_4$, from about 5% wt to about 90% wt $C_5$, from about 5% wt to about 90% wt $C_6$, and from about 5% wt to about 90% wt $C_7$ and heavier hydrocarbons. The $C_4$ hydrocarbons can include isobutene, isobutane, butane, butene, derivatives thereof or combinations thereof. In one or more embodiments, the first product via line 132 can have an isobutane to isobutene molar ratio ranging from about 1:1 to about 1.5:1. The temperature of the first product can be from about 10° C. to about 100° C. lower than the temperature of the dehydrogenation feed via line 128, as the dehydrogenation reaction is endothermic. In one or more embodiments, the first product can include about 90% or more wt $C_4$. In one or more embodiments, the first product can include about 90% wt or more $C_4$-$C_{10}$ olefins. In one or more embodiments, the first product can include about 40% wt to about 95% wt olefins, and about 5% wt to about 60% wt paraffins.

The dehydrogenation reactions in the one or more dehydrogenation reactors 130 can also produce hydrogen and other non-condensable secondary products which can be present in the first product via line 132. The non-condensable secondary products can include, but are not limited to, $C_1$-$C_3$ hydrocarbons. In one or more embodiments, the first product via line 132 can have a molar ratio of hydrogen to total hydrocarbons ranging from about 0.5:1 to about 2.0:1.

The one or more dehydrogenation reactors 130 can be any system or device or combination of systems and/or devices suitable for dehydrogenating alkanes. In one or more embodiments, the dehydrogenation reactors 130 can employ a thermal process, catalytic process, or any combination thereof, either in series or parallel. In one or more embodiments, the one or more dehydrogenation reactors 130 can operate at pressures ranging from less than 10 kPa to about 300 kPa. Each dehydrogenation reactor 130 can operate at temperatures from about 538° C. to about 649° C., from about 538° C. to about 559° C., from about 538° C. to about 579° C., from about 538° C. to about 599° C., from about 538° C. to about 619° C., or from about 538° C. to about 639° C.

The first product via line 132 can be used as a feedstock via line 178 for subsequent processing and/or further purification. In one or more embodiments, about 5% wt to 25% wt, about 15% wt to 45% wt, about 25% wt to 60% wt, or about 40% wt to 70% wt of the first product via line 132 can be used as feedstock via line 178 and the balance, if any, can be further processed to provide purified isobutenes and isobutanes via line 152. In one or more embodiments, about 25% wt to 55% wt, about 45% wt to 70% wt, about 55% wt to 85% wt, about 65% wt to 90% wt, or about 75% wt to 100% wt of the first product can be used as feedstock via line 178 and the balance, if any, can be further processed to provide purified isobutenes and isobutanes via line 152.

In one or more embodiments, all or any portion of the first product via line 132 can be further processed using one or more quench columns 135, absorption columns 145, and/or desorbing columns 150 to provide purified isobutenes and isobutanes via line 152. In one or more embodiments, the first product via line 132 can be introduced to one or more quench columns 135 where the temperature of the first product can be reduced by direct contact with a heat transfer fluid, such as water, to reduce or stop the rate of dehydrogenation. The quench column 135 can be any device, system or combination of systems and/or devices suitable for reducing the temperature of a hydrocarbon to provide a cooled $C_4$ mixture via line 136. In one or more embodiments, the quench column 135 can include packing media to provide additional surface area to facilitate thermal contact between the first product via line 132 and the heat transfer medium, such as water. Each quench column 135 can include one or more rings, saddles, balls, irregular sheets, tubes, spirals, trays, and/or baffles. In one or more embodiments, the cooled $C_4$ mixture via line 136 can have a temperature ranging from about 10° C. to about 500° C.; about 50° C. to about, 400° C.; or about 100° C. to about 300° C.

The cooled $C_4$ mixture can be compressed using one or more compressors 140 to provide a compressed $C_4$ mixture via line 142. The compressor 140 can include any device, system or combination of systems and/or devices suitable for compressing a gas, liquid, and/or multi-phase fluid to provide the compressed $C_4$ mixture. For example, the compressor 140 can include one or more reciprocating, rotary, axial flow, centrifugal, diagonal or mixed-flow, scroll, or diaphragm compressors or any combination thereof. In one or more embodiments, the compressor 140 can have multiple compressor stages. In one or more embodiments, the compressor 140 can have intercooling between one or more compressor stages. In one or more embodiments, the compressor 140 can compress the cooled $C_4$ mixture via line 136 to a pressure of about 800 kPa to about 1500 kPa. In one or more embodiments, the temperature of the compressed $C_4$ mixture can be from about 10° C. to about 200° C.

In one or more embodiments, the compressed $C_4$ mixture via line 142 can be separated from hydrogen and the other non-condensables within one or more absorption columns 145. The absorption column 145 can include packing media to facilitate gas liquid separation and physical contact between the compressed $C_4$ mixture and a solvent. The packing media can include saddles, balls, irregular sheets, tubes, spirals, trays, and baffles. The hydrogen and non-condensables can exit the absorption column 145 via line 146. The $C_4$ compounds and any heavier hydrocarbons, if present, can exit with the solvent via bottoms 148. In one or more embodiments, the bottoms exiting the absorption column 145 can include from about 10% vol to about 60% vol $C_4$ compounds. The balance can contain solvent and heavier hydrocarbons, if present. In one or more embodiments, the column 145 can be operated at a temperature of from about 10° C. to about 200° C. at pressures ranging from about 200 kPa to about 2000 kPa.

The solvent mixture via line 148 can be introduced to the one or more desorbing columns 150 where at least a portion of the isobutenes and isobutanes can be evolved by heating the solvent mixture to provide isobutenes and isobutanes via line 152 and recovered solvent via line 154. The solvent can be recycled to the absorption column 145 via line 154.

The desorbing column 150 can be any device, system or combination of systems and/or devices suitable for selectively separating dissolved isobutenes and isobutanes from the solvent. In one or more embodiments, the desorbing column 150 can include packing media to facilitate the selective separation. For example, each desorbing column 150 can include one or more saddles, balls, irregular sheets, tubes, spirals, trays, and/or baffles. In one or more embodiments, the isobutene concentration via line 152 can be at least 15% vol, 25% vol, 35% vol, 45% vol, 55% vol, or 65% vol. In one or more embodiments, the isobutane concentration via line 152 can be at least 30% vol, 40% vol, 50% vol, 60% vol, 70% vol, or 80% vol.

In one or more embodiments, all or any portion of the isobutenes and isobutanes via line 152 can be combined with methanol and etherified to provide MTBE product. In one or more embodiments, all or any portion of the isobutenes and isobutanes via line 152 can bypass the MTBE step and combined with the first product via line 132 to provide the feedstock via line 178. In one or more embodiments, a portion ranging from about 1% wt, 10% wt, 25% wt, 35% wt, or 50% wt to about 60% wt, 70% wt, 80%, 95% wt, or 100% wt of the isobutenes and isobutanes via line 152 can be directed to the feedstock via line 178 and the balance to the MTBE unit. In one or more embodiments, a portion ranging from about 40% wt, 50% wt, or 60% wt to about 90% wt, 95% wt, or 99% wt of the isobutenes and isobutanes via line 152 can be directed to the feedstock via line 178 and the balance to the MTBE unit. In one or more embodiments, all of the isobutenes and isobutanes via line 152 can be directed to the feedstock via line 178, thereby completely bypassing the MTBE unit.

In one or more embodiments, the MTBE unit can include one or more etherification reactors 155 and two or more pressure columns 160, 165. One or more methanol units 170, using the $C_1$-$C_3$ hydrocarbons via line 106 as a feedstock, can be used to supply the methanol to the MTBE unit via line 172. The methanol via line 172 can have a temperature from about 10° C. to about 100° C. and a pressure from about 200 kPa to about 2000 kPa.

In one or more embodiments, at least a portion of the methanol via line 172 can be combined with the isobutenes and isobutanes via line 152 to provide an etherification feed via line 153. In one or more embodiments, the etherification feed can include a methanol-to-isobutene molar ratio of about 0.9:1 to about 1.5:1. In one or more embodiments, the etherification feed can include up to about 20% wt isobutane, up to about 20% wt $C_5$ and heavier hydrocarbons, or about 10% wt ether. In one or more embodiments, the etherification feed can include about 80% wt, about 90% wt, or about 99% wt methanol.

The etherification feed via line 153 can be heated (not shown) and introduced to the one or more etherification reactors 155 wherein at least a portion of the methanol and isobutene can react to form raw MTBE via line 156. By "raw MTBE" it is meant that the MTBE can include one or more contaminants such as isobutane and methanol. In one or more embodiments, the raw MTBE can include at least about 80% wt, at least about 90% wt, or at least about 98% wt MTBE, up to about 20% wt methanol, and up to about 20% wt isobutane. In one or more embodiments, the raw MTBE can include from about 80% wt to about 98% wt MTBE.

The etherification reactors 155 can include a fixed catalyst bed. In one or more embodiments, the fixed catalyst bed can have a solid bed of sulfonated ion exchange resins. In one or more embodiments, the etherification reaction can take place at temperatures from about 30° C. to about 100° C., from about 30° C. to about 60° C., or from about 60° C. to about 90° C. The etherification reaction can occur at pressures from about 200 kPa to about 2400 kPa or from about 1000 kPa to about 2400 kPa. In one or more embodiments, the molar ratio of methanol to isobutene can be maintained from about 1:1 to about 2:1; from about 1.1:1 to about 1.4:1.

The raw MTBE via line 156 can be selectively separated using one or more pressure columns ("first pressure column") 160 to provide isobutane via line 162 and a MTBE mixture via line 164. In one or more embodiments, the MTBE mixture can include MTBE and methanol. In one or more embodiments, all or any portion of the isobutane via line 162 can be recycled to the one or more dehydrogenation reactors 130. For example, about 1% wt to 35% wt, about 1% wt to 55% wt, about 1% wt to 75% wt, or about 1% wt to 100% wt of the isobutane via line 162 can be recycled to the one or more dehydrogenation reactors 130. In one or more embodiments, at least the recycled isobutane via line 162 and the warm isobutane via line 126 can be combined and introduced to the one or more dehydrogenation reactors 130 via line 128.

The first pressure column 160 can include any device or system or combination of devices and/or systems suitable for selectively separating the raw MTBE line 156 to provide isobutane via line 162 and the MTBE mixture via line 164. The first pressure column 160 can operate at temperatures ranging from about 10° C. to about 200° C. In one or more embodiments, the first pressure column 160 can operate at pressures ranging from about 200 kPa to about 2000 kPa. The first pressure column 160 can include packing media to facilitate the separation of the raw MTBE product via line 156. For example, each pressure column 160 can include saddles, balls, irregular sheets, tubes, spirals, trays, and/or baffles.

The MTBE mixture via line 164 can be selectively separated using one or more pressure columns ("second pressure column") 165 to provide a methanol product via line 166 and an MTBE product via line 168. In one or more embodiments, the methanol product can include one or more methanol/MTBE azeotropes. The second pressure column 165 can operate at temperatures ranging from about 10° C. to about 200° C. In one or more embodiments, the second pressure column 165 can operate at pressures ranging from about 200 kPa to about 2000 kPa. In one or more embodiments, the methanol product via line 166 can include a methanol/ether azeotrope. The methanol product via line 166 can include up to 20% wt methanol and up to 20% wt water. Like the first pressure columns first pressure 160, the columns second pressure 165 can include one more saddles, balls, irregular sheets, tubes, spirals, trays, and/or baffles to facilitate separation therein.

In one or more embodiments, all or any portion of the methanol product via line 166 can be recycled to the etherification reactor 155 via line 153. For example, about 1% wt to 35% wt, about 1% wt to 55% wt, about 1% wt to 75% wt, or about 1% wt to 100% wt of the methanol product can be combined with the feed via line 153. In one or more embodiments, about 1% wt to 15% wt, about 15% wt to 35% wt, about 25% wt to 60% wt, about 35% wt to 75% wt, or about 55% wt to 99% wt of the methanol product can be recycled to the one or more etherification reactors 155.

In one or more embodiments, one or more hydrocarbons can be recycled ("first recycle") via line 194 from one or more downstream cracking and/or fractionation systems as described hereinafter with reference to FIG. 2. In one or more embodiments, at least a portion of the hydrocarbons via line 194 can be recycled to the one or more dehydrogenation reactors 130. In one or more embodiments, at least a portion of the hydrocarbons via line 194 can be recycled to the fractionator 105 via line 102. For example, at least 35% wt to 65% wt, 45% wt to 85% wt, 55% wt to 95% wt, or 75% wt to 100% wt of the $C_4$ hydrocarbons via line 194 can be recycled to the fractionator 105. In one or more embodiments, at least 10% wt to 99% wt, 25% wt to 99% wt, 50% wt to 99% wt, or 75% wt to 99% wt of the hydrocarbons via line 194 can be recycled to the fractionator 105 via line 102. In one or more embodiments, at least a portion of the hydrocarbons via line 194 can be recycled to the rectifier column 105 via line 102, and the balance recycled to the one or more dehydrogenation reactors 130 via line 126. For example, at least 35% wt to 65% wt, 45% wt to 85% wt, 55% wt to 95% wt, or 75% wt to 100% wt of the hydrocarbons via line 194 can be recycled to the dehydrogenation reactors 130 via line 126. In one or more embodiments, at least 10% wt to 99% wt, 25% wt to 99% wt, 50% wt to 99% wt, or 75% wt to 99% wt of the hydrocarbons via line 194 can be recycled to the dehydrogenation reactors 130 via line 126.

Although not shown in FIG. 1, at least a portion of the hydrocarbons via line 194 can be recycled to the first product via line 132. At least 1% wt to 35% wt, at least 1% wt to 45% wt, at least 1% wt to 55% wt, at least 1% wt to 75% wt, or at least 1% wt to 99% wt of the hydrocarbons via line 194 can be recycled to the first product via line 132. In one or more embodiments, the hydrocarbons via line 194 can include both butanes and isobutanes. The hydrocarbons via line 194 can include from about 20% vol to about 80% vol butane. In one or more embodiments, the hydrocarbons can include from about 5% vol to about 20% vol isobutane. In one or more embodiments, the hydrocarbons can have a temperature ranging from about 10° C. to about 200° C. In one or more embodiments, the pressure of the hydrocarbons can range from about 20 kPa to about 400 kPa.

Considering the feedstock via line 178 in more detail, the feedstock via line 178 can include from about 20% vol to about 80% vol isobutene. In one or more embodiments, the feedstock via line 178 can include from about 40% vol to about 70% vol isobutane. In one or more embodiments, the feedstock via line 178 can include about 30% vol to about 60% vol butane and about 40% vol to about 70% vol isobutene. In one or more embodiments, the feedstock via line 178 can include at least 90% wt $C_4$-$C_{10}$ hydrocarbons. In one or more embodiments, the feedstock via line 178 can include a mixture of about 40% wt to about 95% wt $C_4$-$C_{10}$ olefinic hydrocarbons and about 5% wt to about 60% wt $C_4$-$C_{10}$ paraffinic hydrocarbons.

In one or more embodiments, the feedstock via line 178 is essentially vapor. In one or more embodiments, the feedstock via line 178 is at least 99 vol % vapor, the balance being liquid phase. In one or more embodiments, the feedstock via line 178 is at least 95 vol % vapor, the balance being liquid phase. In one or more embodiments, the feedstock via line 178 is at least 90 vol % vapor, the balance being liquid phase.

Figure 2:
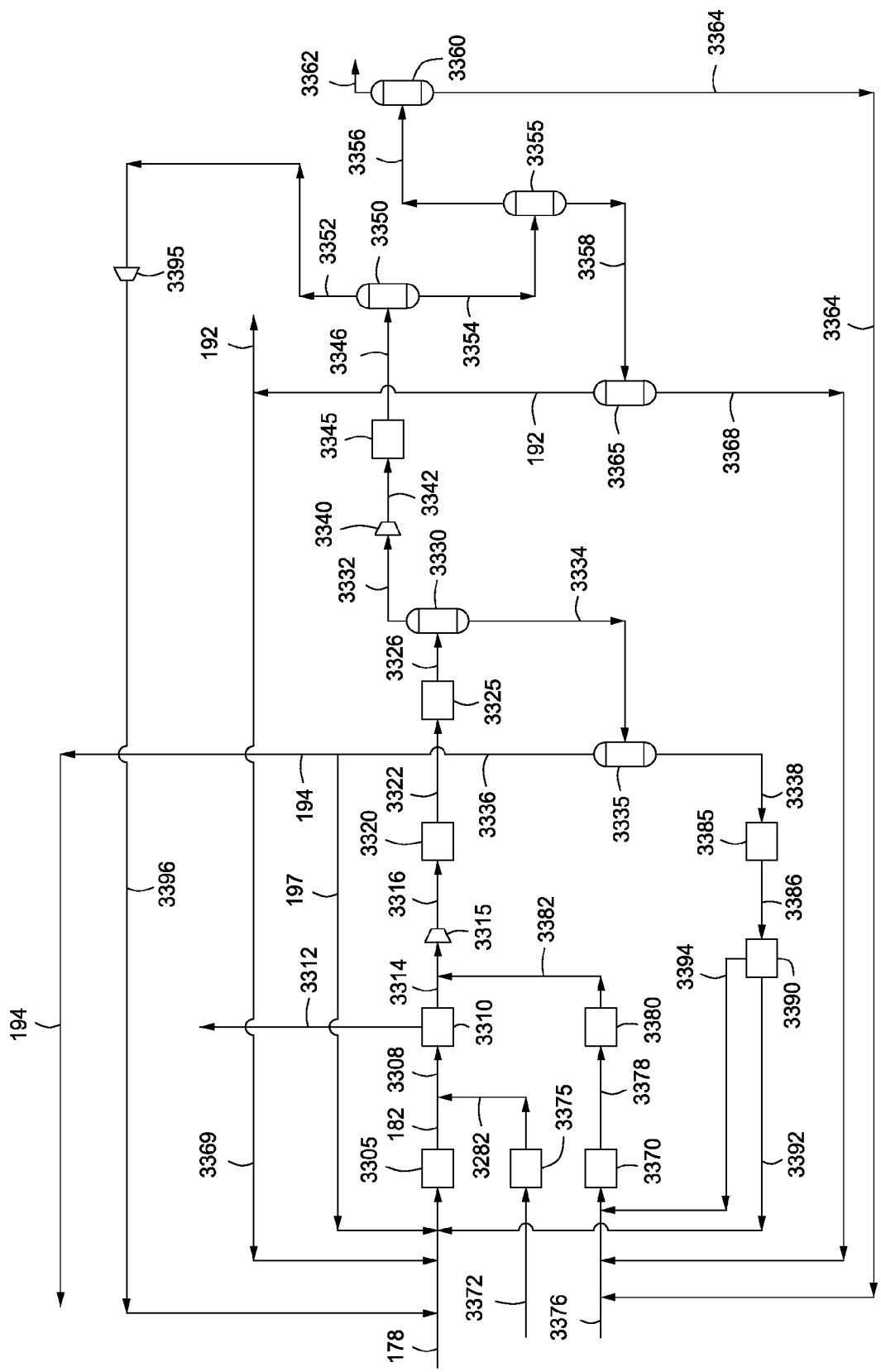
FIG. 2 depicts an illustrative system for producing one or more olefins according to one or more embodiments described.

FIG. 2 depicts an illustrative system for producing one or more olefins according to one or more embodiments. In one or more embodiments, the feedstock via line 178 can be introduced to one or more crackers 3305 and cracked therein to provide a second product via line 182. One or more refinery hydrocarbons and/or light hydrocarbons can be introduced via line 3372 to a fluid catalytic cracker ("FCC") 3375 and cracked therein to provide a cracked hydrocarbon via line 3282. In one or more embodiments, one or more alkanes can be introduced via line 3376 to one or more steam pyrolytic cracker 3370 to provide an olefinic effluent 3378 ("cracked alkanes"). The olefinic effluent 3378 can be cooled using one or more quench columns 3380 to provide a cooled effluent via 3382.

The second product via line 182 and the cracked hydrocarbon via line 3282 can be combined to provide a hydrocarbon mixture via line 3308 (the "first mixture") and fractionated to provide an olefinic mixture via 3314 and a naphthenic mixture via line 3312. The olefinic mixture via 3314 can be combined with the quenched effluent via 3382 (the "second mixture") and purified using one or more purifiers 3320, 3325 and columns 3330, 3335, 3350, 3360, and 3365 to provide multiple products including propylene, ethylene, propane and ethane. Heavier $C_4$-$C_6$ hydrocarbons, separated from the finished products, can be recycled to the $C_4$ production unit (depicted in FIG. 1) via line 194.

The light hydrocarbons can include one or more hydrocarbons having a boiling point within a temperature range from about 220° C. to about 705° C., from about 285° C. to about 645° C., or from about 650° C. to about 705° C. at pressures ranging from about 10 kPa to about 300 kPa. In one or more embodiments, the refinery hydrocarbons can include gas oil, full range gas oil, resid, combination thereof; refinery recycle streams such as decanted oil, heavy catalytic cycle oil, and light catalytic cycle oil, or other refinery recycle streams that are first processed, for example by hydrotreating before use. In one or more embodiments, the refinery and/or light hydrocarbons can be introduced to the one or more fluidized catalytic crackers 3375 at a temperature ranging of about 25° C. to about 300° C. In one or more embodiments, the refinery and/or light hydrocarbons can be pre-heated to temperatures ranging from about 25° C. to about 200° C. prior to cracking.

The alkanes introduced to the steam pyrolytic cracker 3370 can include one or more paraffinic hydrocarbons having two or more carbon atoms. In one or more embodiments, the alkanes can include one or more $C_2$-$C_{12}$ paraffinic hydrocarbons. In one or more embodiments, the one or more alkanes can be introduced to the steam pyrolytic cracker 3370 at a temperature of about 25° C. to about 200° C. In one or more embodiments, the one or more alkanes can be introduced to the steam pyrolytic cracker 3370 at a pressure of about 100 kPa to about 2000 kPa.

The cracked hydrocarbons via line 3282 can include 50% wt, 60% wt, or 70% wt $C_4$-$C_{10}$. In one or more embodiments, the refinery effluent can include from about 1% wt to about 10% wt $C_2$, from about 1% wt to about 20% wt $C_3$, from about 5% wt to about 25% wt $C_4$, from about 5% wt to about 25% wt $C_5$, and from about 30% wt to about 70% wt $C_6$ and heavier hydrocarbons. In one or more embodiments, the refinery effluent can exit the fluidized catalytic cracker 3375 at a temperature of about 400° C. to about 600° C.

In one or more embodiments, the second hydrocarbon mixture via line 3308 can be introduced to one or more fractionators 3310 and selectively separated therein to provide a naphthenic mixture via line 3312 and an olefinic mixture via line 3314. In one or more embodiments, the one or more fractionators 3310 can remove heavy naphtha, light cycle oil, slurry oil, or any combination thereof from the second hydrocarbon mixture to recover the olefinic mixture via line 3314 and the naphthenic mixture via line 3312. In one or more embodiments, the olefinic mixture can include one or more $C_2$-$C_{10}$ olefins.

In one or more embodiments, the naphthenic mixture via line 3312 can include about 40% wt to about 90% wt $C_7$-$C_{12}$ hydrocarbons. In one or more embodiments, the naphtha via line 3312 can include from about 5% wt to about 40% wt $C_7$, from about 5% wt to about 40% wt $C_8$, from about 5% wt to about 20% wt $C_9$, or from about 5% wt to about 10% wt $C_{10}$ and heavier hydrocarbons.

The olefinic mixture via line 3314 can include 20% wt to 90% wt of the one or more $C_2$-$C_{10}$ hydrocarbons. In one or more embodiments, the olefinic mixture can include from about 5% wt to about 30% wt $C_4$, from about 5% wt to about 30% wt $C_5$, from about 5% wt to about 30% wt $C_6$, and from about 5% wt to about 20% wt $C_7$ and heavier hydrocarbons. In one or more embodiments, the olefinic mixture can exit the fractionator 3310 at a pressure of about 100 kPa up to about 500 kPa.

In one or more embodiments, the feed via line 3376 can include ethane, propane, mixtures thereof or combinations thereof. In one or more embodiments, the feed via line 3376 can include from about 70% wt, 80% wt, or 90% wt $C_2$-$C_3$ alkanes. In one or more embodiments, the feed via line 3376 can be introduced to the convection zone of the steam pyrolytic cracker 3370 at a temperature of about 100° C. to about 300° C. The alkane feed can be heated in the convection zone of the steam pyrolytic cracker 3370 to a temperature of about 400° C. to about 700° C. In one or more embodiments, the alkane feed can be partially vaporized in the convection zone. For example, at least 10% wt, 20% wt, 30% wt, 40% wt, or 50% wt of the alkane feed can be vaporized in the convection zone of the steam pyrolytic cracker 3370. In one or more embodiments, at least 55% wt, 65% wt, 75% wt, 85% wt, 95% wt, or 100% wt of the alkane feed can be vaporized in the convection zone of the steam pyrolytic cracker 3370. In one or more embodiments, the cracked alkane via line 3382 can include about 20% wt to about 60% wt ethane and about 5% wt to about 30% wt propane.

The quench column 3380 can be any device suitable for reducing the temperature of the cracked hydrocarbon mixture in line 3378 produced by the cracker 3370. In one or more embodiments, reducing the temperature of the cracked hydrocarbon can reduce or stop the rate of hydrocarbon cracking. The quench column 3380 can include packing media to provide surface area for the cracked alkanes and a heat transfer medium to make thermal contact. For example, the packing media can include rings, saddles, balls, irregular sheets, tubes, spirals, trays, baffles, or any combination thereof. In one or more embodiments, the cooled hydrocarbons can exit the quench column 3380 via line 3382 at a temperature from about 25° C. to about 100° C.

In one or more embodiments the hydrocarbons via line 3382 can be combined with the olefinic mixture via line 3314 and compressed using one or more compressors 3315. The compressed olefinic mixture via line 3316 can exit the one or more compressors 3315 at pressures ranging from about 500 kPa to about 3000 kPa. In one or more embodiments, the pressure of the compressed olefinic mixture can be about 500 kPa to 3000 kPa or from about 500 kPa to 1000 kPa. In at least one specific embodiment, the compressed olefinic mixture can have a temperature of about 40° C. up to about 300° C.

In one or more embodiments, the compressed olefinic mixture via line 3316 can be treated using one or more treating units 3320 to remove oxygenates, acid gases, water, or any combination thereof to provide a treated olefinic mixture via line 3322. In one or more embodiments, the treated olefinic mixture via line 3322 can include less than about 500 ppmv $H_2S$, less than about 50 ppmv $H_2S$, or less than about 1 ppmv $H_2S$. In one or more embodiments, the treated olefinic mixture can include less than about 500 ppmv $CO_2$, less than about 100 ppmv $CO_2$, or less than about 50 ppmv $CO_2$.

In one or more embodiments, the treated olefinic mixture via line 3322 can be dried in one or more drying units 3325 to provide dried olefinic mixture via line 3326. The dried olefinic mixture can include less than 100 ppmv $H_2O$, less than 10 ppmv $H_2O$, or less than 0.1 ppmv $H_2O$. In one or more embodiments, the dried olefinic mixture can include less than 5 ppmv $H_2O$, less than 1 ppmv $H_2O$, or less than 0.5 ppmv $H_2O$.

In one or more embodiments, the dried olefinic mixture via line 3326 can be introduced to one or more de-propanizers 3330 and selectively separated therein to provide an overhead containing $C_3$ and lighter hydrocarbons via line 3332, and a bottoms containing $C_4$ and heavier hydrocarbons via line 3334. In one or more embodiments, the $C_3$ and lighter hydrocarbons via line 3332 can include 90% wt, 95% wt, or 99% wt $C_3$ and lighter hydrocarbons. In one or more embodiments, the $C_3$ and lighter hydrocarbons can include hydrogen. The $C_3$ and lighter hydrocarbons can include from about 10% wt to about 40% wt $C_2$, from about 20% wt to about 70% wt $C_3$, and from about 0.1% wt to about 1% wt $H_2$. The $C_3$ and lighter hydrocarbons via line 3332 can exit the de-propanizer 3330 at a pressure of about 500 kPa up to about 2500 kPa. In one or more embodiments, the pressure of the $C_3$ and lighter hydrocarbons via line 3332 can be from about 500 kPa to about 1000 kPa.

The $C_4$ and heavier hydrocarbons via line 3334 can include 90% wt, 95% wt, or 99% wt $C_4$-$C_{10}$ hydrocarbons. In one or more embodiments, the $C_4$ and heavier hydrocarbons via line 3334 can include from about 30% wt to about 80% wt $C_4$, from about 5% wt to about 30% wt $C_5$, from about 5% wt to about 20% wt $C_6$, and from about 5% wt to about 20% wt $C_7$ and heavier hydrocarbons.

In one or more embodiments, the $C_4$ and heavier hydrocarbons via line 3334 can be introduced to one or more gasoline splitters 3335 and selectively separated therein to provide an overhead containing $C_4$-$C_6$ hydrocarbons via line 3336, and bottoms containing $C_7$ and heavier hydrocarbons via line

3338. In one or more embodiments, the $C_7$ and heavier hydrocarbons can include about 80% wt, 90% wt, or 95% wt $C_4$-$C_6$, and from about 5% wt to about 80% wt $C_7$ and heavier hydrocarbons. In one or more embodiments, the $C_7$ and heavier hydrocarbons can include from about 40% wt to about 80% wt $C_4$, from about 5% wt to about 60% wt $C_5$, from about 1% wt to about 30% wt $C_6$, from about 1% wt to about 20% wt $C_7$, and from about 1% to about 10% wt $C_8$ and heavier hydrocarbons.

In one or more embodiments, all or any portion of the $C_4$-$C_6$ hydrocarbons via line 3336 can be recycled to the cracker 3305 via line 197. For example, at least 55% wt to 65% wt, 65% wt to 75% wt, 75% wt to 85% wt, or 85% wt to 95% wt of $C_4$-$C_6$ hydrocarbons via line 3336 can be recycled to the cracker 3305 via line 197. In one or more embodiments, at least 10% wt to 20% wt, 20% wt to 30% wt, 30% wt to 40% wt, or 40% wt to 50% wt of the $C_4$-$C_6$ hydrocarbons via line 3336 can be recycled to the cracker 3305 via line 197. In one or more embodiments, at least a portion of the $C_4$-$C_6$ hydrocarbons via line 197 can be combined with the feedstock via line 178. In one or more embodiments, at least 10% wt to 20% wt, 20% wt to 30% wt, 30% wt to 40% wt, or 40% wt to 50% wt of $C_4$-$C_6$ hydrocarbons via line 197 can be combined with the feedstock via line 178. In one or more embodiments, at least 5% wt to 35% wt, at least 15% wt to 55% wt, at least 45% wt to 70% wt, at least 60% wt to 85% wt, or at least 75% wt to 100% wt of the $C_4$-$C_6$ hydrocarbons via line 197 can be combined with feedstock via line 178.

In one or more embodiments, all or any portion of the $C_4$-$C_6$ hydrocarbons via line 3336 can be recycled to the one or more dehydrogenation reactors 130 (FIG. 1) via the first recycle in line 194. For example, at least 55% wt to 65% wt, 65% wt to 75% wt, 75% wt to 85% wt, or 85% wt to 95% wt of the $C_4$-$C_6$ hydrocarbons via line 3336 can be recycled to the one or more dehydrogenation reactors 130 via line 194. In one or more embodiments, at least 10% wt to 20% wt, 20% wt to 30% wt, 30% wt to 40% wt, or 40% wt to 50% wt of the $C_4$-$C_6$ hydrocarbons via line 3336 can be recycled to the one or more dehydrogenation reactors 130 via line 194.

In one or more embodiments, the $C_4$-$C_6$ hydrocarbons via line 3336 can include n-butanes and isobutanes. The $C_4$-$C_6$ hydrocarbons can include from about 10% wt to about 50% wt n-butanes. In one or more embodiments, the $C_4$-$C_6$ hydrocarbons can include from about 10% wt to about 50% wt isobutanes. The $C_4$-$C_6$ hydrocarbons via line 3336 can include $C_4$-$C_6$ olefins from about 50% wt to about 90% wt $C_4$-$C_6$ olefins. In one or more embodiments, the $C_4$-$C_6$ hydrocarbons via line 3336 can include from about 10% wt to about 50% wt $C_4$ olefins, from about 10% wt to about 50% wt $C_5$ olefins, and from about 5% wt to about 30% wt $C_6$ olefins.

In one or more embodiments, the $C_7$ and heavier hydrocarbons via line 3338 can be stabilized using one or more gasoline hydrotreaters 3385 to provide a treated gasoline via line 3386. In one or more embodiments, the treated gasoline can include from about 70% wt, 80% wt, or 90% wt $C_6$ and heavier hydrocarbons. In one or more embodiments, the treated gasoline can include from about 75% wt to about 85% wt $C_6$, from about 15% wt to about 25% wt $C_7$, and from about 5% wt to about 10% wt $C_8$ and heavier hydrocarbons The treated gasoline can be selectively separated using one or more benzene/toluene/xylene ("BTX") units 3390 to separate the aromatics into line 3392, and a raffinate in line 3394. In one or more embodiments, the aromatics via line 3392 can include 40% wt, 50% wt, 60% wt, 70% wt, or even 80% wt BTX. The aromatics can include from about 10% wt to about 40% wt benzene, from about 20% wt to about 60% wt toluene, and from about 10% wt to about 40% wt xylene. In one or more embodiments, all or any portion of the aromatics via line 3392 can be directly recycled to the one or more crackers 3305 or be recycled to the one or more crackers 3375 via line 178. In one or more embodiments, at least 10% wt, 20% wt, 30% wt, or 40% wt of the aromatics can be recycled to the cracker 3305. In at least one specific embodiment, 10% wt, 15% wt, or 20% wt of the aromatics can be recycled to the cracker 3305.

In one or more embodiments, the raffinate via line 3394 can be lean in aromatics. For example, the raffinate can include less than about 40% wt, 30% wt, 20% wt, or 10% wt BTX. All or part of the raffinate via line 3394 can be recycled directly to the steam pyrolytic cracker 3370 or combined with the feed via 3376 prior to the cracker 3370. In one or more embodiments, at least 20% wt, 30% wt, 40% wt, or 50% wt of the raffinate can be recycled to the steam pyrolytic cracker 3370. In one or more embodiments, at least 70% wt, 80% wt, or 90% wt of the raffinate can be recycled to the steam pyrolytic cracker 3370.

In the de-propanizer 3330, the $C_3$ and lighter hydrocarbons exiting via line 3332 can be compressed using one or more compressors 3340. In one or more embodiments, compressing the $C_3$ and lighter hydrocarbons can facilitate the separation of lighter hydrocarbons from the heavier hydrocarbons via line 3332. The compressed $C_3$ and lighter hydrocarbons exiting the one or more compressors 3340 via line 3342 can have a pressure of about 500 kPa to about 3500 kPa. In one or more embodiments, the compressed $C_3$ and lighter hydrocarbons can exit the one or more compressors 3340 at a pressure of about 500 kPa to about 1500 kPa. The compressed $C_3$ and lighter hydrocarbons can exit the one or more compressors 3340 at a temperature of about 5° C. to about 100° C.

The compressed $C_3$ and lighter hydrocarbons via line 3342 can be chilled using one or more chill trains 3345 to provide chilled $C_3$ and lighter hydrocarbons via line 3346. The chilled $C_3$ and lighter hydrocarbons can exit the one or more chill trains 3345 at a temperature of about −40° C. to about 40° C. In one or more embodiments, the chilled $C_3$ and lighter hydrocarbons can have a temperature from about −20° C. to about 5° C. Recovered ethane and propane from the system can be used as refrigerant to the one or more chill trains 3345.

The chilled $C_3$ and lighter hydrocarbons can be introduced to one or more de-methanizers 3350 and selectively separated therein to provide an overhead containing methane via line 3352 and a bottoms containing $C_2$ and $C_3$ hydrocarbons via line 3354. In one or more embodiments, the overhead 3352 can include from about 50% mol to about 95% mol methane. In one or more embodiments, the overhead 3352 can include 70% mol, 80% mol, or 90% mol methane. In one or more embodiments, the pressure of the overhead 3352 can range from about 300 kPa to about 1000 kPa. In one or more embodiments, the bottoms 3354 can include from about 20% wt to about 50% wt $C_2$ and from about 40% wt to about 80% wt $C_3$.

In one or more embodiments, the methane via line 3352 can be recycled to the cracker 3305 via line 178. In one or more embodiments, the methane exiting the de-methanizer 3350 can be compressed using one or more compressors 3395 to provide a compressed methane via line 3396 which can be recycled to the one or more crackers 3305 via line 178, as shown. In one or more embodiments, 15% vol to 35% vol; 20% vol to 35% vol; 25% vol to 35% vol; or 30% vol to 35% vol of the methane via line 3352 can be recycled to the cracker 3305. The compressed methane via line 3396 can have at a pressure of about 100 kPa to about 1000 kPa, and a temperature of about 25° C. to about 200° C.

The C$_2$ and C$_3$ hydrocarbons via line 3354 can be introduced to one or more de-ethanizers 3355 and selectively separated therein to provide an overhead containing a C$_2$ hydrocarbon mixture via line 3356 and a bottoms containing a C$_3$ hydrocarbon mixture via line 3358. In one or more embodiments, the overhead 3356 can include about 90% mol, 95% mol, or 99% mol C$_2$. In one or more embodiments, the overhead 3356 can include from about 5% mol to about 70% mol ethane and from about 30% mol to about 95% mol ethylene. In one or more embodiments, the bottoms 3358 can include about 90% mol, 95% mol, or 99% mol C$_3$. In one or more embodiments, the bottoms 3358 can include from about 5% mol to about 30% mol propane and from about 70% mol to about 95% mol propylene.

In one or more embodiments, the C$_2$ hydrocarbon mixture via line 3356 can be introduced to one more C2 splitters 3360 and selectively separated therein to provide an overhead ("ethylene product") via line 3362 and a bottoms ("ethane product") via line 3364. In one or more embodiments, overhead 3362 can include about 90% mol, 95% mol, or 99% mol ethylene. In one or more embodiments, the overhead 3362 can include about 95% mol, 99% mol, or 99.9% mol ethylene. The bottoms 3364 can include 90% mol, 95% mol, or 99% mol ethane. In one or more embodiments, the bottoms 3364 can include about 95% mol, 99% mol, or 99.9% mol ethane.

In one or more embodiments, the C$_3$ hydrocarbon mixture via line 3358 can be introduced to one or more C3 splitters 3365 and selectively separated therein to provide an overhead ("third product" or "propylene product") via line 192 and a bottoms ("propane product") via line 3368. In one or more embodiments, the bottoms 3368 can include about 90% mol, 95% mol, or 99% mol propane. The overhead 192 can include 80 mol %, 90 mol %, or 99 mol % propylene.

In one or more embodiments, all or any portion of the propylene product via line 192 can be recycled via line 3369 to the one or more crackers 3305. Recycling at least a portion of the propylene product can suppress propylene production in the one or more crackers 3305, thereby increasing ethylene production (i.e. ethylene yield). In one or more embodiments, about 10% vol to 60% vol; 20% vol to 60% vol; 30% vol to 60% vol; 40% vol to 60% vol; or 50% vol to 60% vol of the propylene product via line 192 can be recycled to the one or more crackers 3305. In one or more embodiments, at least 60% vol to 100% vol; 70% vol to 100% vol; 80% vol to 100% vol; or 90% vol to 100% vol of the propylene product can be recycled to the one or more crackers 3305.

In one or more embodiments, all or any portion of the ethane product via line 3364 can be recycled to the one or more steam pyrolytic crackers 3370 via line 3376. In one or more embodiments, all or any portion of the propane product via line 3368 can be recycled to the one or more steam pyrolytic crackers 3370 via line 3376. For example, about 60% vol to 100% vol; 70% vol to 100% vol; 80% vol to 100% vol; or 90% vol to 100% vol of the ethane product via line 3364 and at least 70% vol to 100% vol; 80% vol to 100% vol; or 90% vol to 100% vol of the propane product via line 3368 can be recycled to the one or more steam pyrolytic crackers 3370, either directly or via line 3376. In one or more embodiments, about 15% vol to 55% vol; 25% vol to 55% vol; 35% vol to 55% vol; or 45% vol to 55% vol of the propane product via line 3368 can be recycled to the one or more steam pyrolytic crackers 3370. In at least one specific embodiment, about 15% vol to 45% vol; 25% vol to 45% vol; or 35% vol to 45% vol of the ethane product via line 3364 can be recycled to the one or more steam pyrolytic crackers 3370.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim 1s not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for making propylene, comprising:
   dehydrogenating a feed comprising butane to provide a first product comprising butene;
   bypassing the first product around an etherification reactor for converting isobutylene to methyl tert-butyl ether;
   cracking at least a portion of the first product in a first cracker to provide a second product comprising propylene, ethylene, and butane;
   cracking a refinery hydrocarbon comprising gas oil, full range gas oil, resid, or a combination thereof in a second cracker to provide a cracked hydrocarbon comprising ethylene, propylene, or a combination thereof;
   cracking one or more alkanes in a third cracker to provide an effluent comprising ethylene and propylene;
   combining the second product, cracked hydrocarbon, and effluent to form a mixture;
   selectively separating at least a portion of the mixture to provide a third product comprising propylene and a first recycle comprising butane; and
   recycling at least a portion of first recycle to the first product.

2. The process of claim 1, wherein the first product is heated to a temperature of about 90° C. to about 370° C.

3. The process of claim 1, wherein cracking at least a portion of the first product occurs at a temperature of about 590° C. to about 675° C., and a pressure of about 40 kPa to about 700 kPa.

4. The process of claim 1, wherein the feed comprises a mixture having from about 40% to about 95% by weight paraffins having 4 or more carbon atoms and about 5% to about 60% by weight olefins having 4 or more carbon atoms.

5. The process of claim 1, wherein the first product comprises a mixture having from about 40% to about 95% by weight olefins having 4 or more carbon atoms and about 5% to about 60% by weight paraffins having 4 or more carbon atoms.

6. The process of claim 1, wherein the first cracker is a fluidized catalytic cracker having a catalyst-to-first product ratio of about 5:1 to about 70:1.

7. The process of claim 1, wherein the second product exits the first cracker at a temperature of from about 550° C. to about 650° C. when the first product comprises at least 90% by weight hydrocarbons having 4 carbon atoms.

8. A process for making propylene, comprising:
dehydrogenating a feed comprising butane to provide a first product comprising butene;
bypassing the first product around an etherification reactor for converting isobutylene to methyl tert-butyl ether;
cracking at least a portion of the first product in a first cracker to provide a second product comprising propylene, ethylene, and butane;
cracking a refinery hydrocarbon comprising gas oil, full range gas oil, resid, or a combination thereof in a second cracker to provide a cracked hydrocarbon comprising ethylene, propylene, or a combination thereof;
cracking one or more alkanes in a third cracker to provide an effluent comprising ethylene and propylene;
combining the second product, cracked hydrocarbon, and effluent to form a mixture;
selectively separating at least a portion of the mixture to provide a third product comprising propylene and a first recycle comprising butane;
recycling at least a portion of the first recycle to the first product; and
recycling at least a portion of the first recycle to the feed.

9. The process of claim 8, wherein cracking at least a portion of the first product occurs at a temperature of about 590° C. to about 675° C., and a pressure of about 40 kPa to about 700 kPa.

10. The process of claim 8, wherein the feed comprises a mixture having from about 40% to about 95% by weight paraffins having 4 or more carbon atoms and about 5% to about 60% by weight olefins having 4 or more carbon atoms.

11. The process of claim 8, wherein the first product comprises a mixture having from about 40% to about 95% by weight olefins having 4 or more carbon atoms and about 5% to about 60% by weight paraffins having 4 or more carbon atoms.

12. The process of claim 8, wherein the first cracker is a fluidized catalytic cracker having a catalyst-to-first product ratio of about 5:1 to about 70:1.

13. The process of claim 8, wherein the second product stream exits the first cracker at a temperature of from about 550° C. to about 650° C. when the first product comprises at least 90% by weight hydrocarbons having 4 carbon atoms.

14. A process for retrofitting a methyl tert-butyl ether process, comprising:
bypassing a first product produced by dehydrogenating a feed comprising butane around an etherification reactor for converting isobutylene to methyl tert-butyl ether, wherein the first product comprises butene;
cracking at least a portion of the first product in a first cracker to provide a second product comprising propylene, ethylene, and butane;
cracking a refinery hydrocarbon comprising gas oil, full range gas oil, resid, or a combination thereof in a second cracker to provide a cracked hydrocarbon comprising ethylene, propylene, or a combination thereof;
cracking one or more alkanes in a third cracker to provide an effluent comprising ethylene and propylene;
combining the second product, cracked hydrocarbon, and effluent to form a mixture;
selectively separating at least a portion of the mixture to provide a third product comprising propylene and a first recycle comprising butane; and
recycling at least a portion of first recycle to the first product.

15. The process of claim 14, wherein the first product is heated to a temperature of about 90° C. to about 370° C.

16. The process of claim 14, wherein cracking at least a portion of the first product occurs at a temperature of about 590° C. to about 675° C., and a pressure of about 40 kPa to about 700 kPa.

17. The process of claim 14, wherein the feed comprises a mixture having from about 40% to about 95% by weight paraffins having 4 or more carbon atoms and about 5% to about 60% by weight olefins having 4 or more carbon atoms.

18. The process of claim 14, wherein the first product comprises a mixture having from about 40% to about 95% by weight olefins having 4 or more carbon atoms and about 5% to about 60% by weight paraffins having 4 or more carbon atoms.

19. The process of claim 14, wherein the first cracker is a fluidized catalytic cracker having a catalyst-to-first product ratio of about 5:1 to about 70:1.

20. The process of claim 14, wherein the second product stream exits the first cracker at a temperature of from about 550° C. to about 650° C. when the first product comprises at least 90% by weight hydrocarbons having 4 carbon atoms.

21. The process of claim 1, wherein the feed further comprises isobutane and has an isobutane concentration of about 50% vol to about 99% vol.

22. The process of claim 1, wherein the feed further comprises about 70% vol or more isobutane and about 5% vol to about 30% vol butane.

23. The process of claim 1, wherein the first product further comprises isobutane, isobutene, hydrogen, and $C_1$ to $C_3$ hydrocarbons, and the process further comprises:
contacting at least a portion of the first product with a solvent to provide a solvent mixture; and
separating the solvent mixture to produce a purified isobutane/isobutene mixture, wherein the purified isobutane/isobutene mixture contains less hydrogen and $C_1$ to $C_3$ hydrocarbons than the first product, and wherein at least a portion of the purified isobutane/isobutene mixture is cracked in the first cracker to provide the second product.

24. The process of claim 1, wherein the feed further comprises about 70% vol or more isobutane and about 5% vol to about 30% vol butane, wherein the first product further comprises isobutene and isobutane and has an isobutane to isobutene molar ratio ranging from about 1:1 to about 1.5:1, and wherein the first recycle further comprises isobutane and has a concentration of isobutane of about 5% vol to about 20% vol and a concentration of butane of about 20% vol to about 80% vol.

25. The process of claim 1, wherein selectively separating at least a portion of the mixture further provides a $C_7$ and heavier product, and the process further comprises hydrotreating the $C_7$ and heavier product to provide a treated gasoline product.

26. The process of claim 25, further comprising:
selectively separating the treated gasoline product to provide an aromatic-rich product comprising about 40 wt % or more aromatics and an aromatic-lean product comprising less than about 30 wt % aromatics;
recycling at least a portion of the aromatic-lean product to the third cracker; and
recycling at least a portion of the aromatic-rich product to the first cracker.

27. The process of claim 1, wherein selectively separating at least a portion of the mixture further provides a second recycle and an third recycle, wherein the second recycle comprises about 90 mol % or more propane and the third recycle comprises about 90 mol % or more ethane, and the process further comprises recycling at least a portion of the second recycle and at least portion of the third recycle to the third cracker.

28. The process of claim 1, wherein selectively separating at least a portion of the mixture further provides a methane recycle comprising about 70 mol % or more methane, and the process further comprises recycling at least a portion of the methane recycle to the first cracker.

29. The process of claim 1, further comprising recycling at least a portion of the third product to the first cracker.

30. The process of claim 1, wherein the third product comprises abut 80 mol % or more propylene, and the process further comprises recycling about 10% vol or more of the third product to the first cracker.

* * * * *